(12) United States Patent
Lakshtanov et al.

(10) Patent No.: US 9,341,549 B2
(45) Date of Patent: May 17, 2016

(54) SAMPLE PREPARATION APPARATUS FOR DIRECT NUMERICAL SIMULATION OF ROCK PROPERTIES

(71) Applicant: BP Corporation North America Inc., Naperville, IL (US)

(72) Inventors: Dmitry Lakshtanov, Weybridge (GB); Joanne Fredrich, Houston, TX (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/336,641

(22) Filed: Jul. 21, 2014

(65) Prior Publication Data

US 2015/0185122 A1    Jul. 2, 2015

Related U.S. Application Data

(60) Provisional application No. 61/921,797, filed on Dec. 30, 2013.

(51) Int. Cl.
| | | |
|---|---|---|
| *G01N 1/04* | (2006.01) | |
| *B28D 5/04* | (2006.01) | |
| *B28D 1/08* | (2006.01) | |
| *G01N 1/28* | (2006.01) | |
| *G01N 23/04* | (2006.01) | |
| *B23D 57/00* | (2006.01) | |

(52) U.S. Cl.
CPC ............ *G01N 1/286* (2013.01); *B23D 57/0046* (2013.01); *B28D 1/08* (2013.01); *B28D 5/045* (2013.01); *G01N 1/04* (2013.01); *G01N 23/046* (2013.01); *G01N 2001/2873* (2013.01)

(58) Field of Classification Search
CPC ....... G01N 1/286; G01N 1/04; G01N 23/046; G01N 2001/2873; B28D 5/045; B28D 1/08; B28D 5/04
See application file for complete search history.

(56) References Cited

U.S. PATENT DOCUMENTS

| | | | | |
|---|---|---|---|---|
| 5,839,424 | A | * 11/1998 | Hauser | B28D 5/0088 125/16.01 |
| 6,539,932 | B2 | * 4/2003 | Ohmori | B24B 27/06 125/16.01 |
| 6,920,871 | B2 | * 7/2005 | Bieri | B23D 57/0053 125/16.01 |
| 7,158,609 | B2 | * 1/2007 | Kikuchi | G01N 23/205 378/70 |

(Continued)

OTHER PUBLICATIONS

Fredrich et al., "Predicting macroscopic transport properties using microscopic image data", J. Geophys. Research, vol. 111, paper B03201 (2006), pp. 1-14.

(Continued)

*Primary Examiner* — Dung Van Nguyen
(74) *Attorney, Agent, or Firm* — John L. Wood

(57) ABSTRACT

A sample preparation apparatus and method of preparing a rock sample using such an apparatus, as useful in connection with the digital numerical simulation of properties of the rock. The disclosed apparatus includes a fixably mounted diamond wire cutter. Three linear translation stages are coupled to a specimen holder. One of the translation stages moves the specimen in a direction parallel to the plane of the cutting wire. The other two translation stages move the specimen in different directions from one another, and when actuated together, advance the specimen into the wire for short distances in a direction out of the plane of the cutting wire. Short piecewise linear cuts are made in the specimen, to provide a sample of the desired shape with a small cross-section.

15 Claims, 11 Drawing Sheets

(56) References Cited

U.S. PATENT DOCUMENTS

| | | | | |
|---|---|---|---|---|
| 8,065,995 B2* | 11/2011 | Bakshi | ............... | B28D 5/0076 125/16.01 |
| 8,259,901 B1* | 9/2012 | Kamireddi | ........... | B23D 59/001 378/73 |
| 8,261,730 B2* | 9/2012 | Bakshi | ................... | B08B 3/02 125/13.01 |

OTHER PUBLICATIONS

Lenoir, "Comportement Mecanique et Rupture Dans Les Roches Argileuses Etudies Par Micro Tomographie a Rayons X", L'Universite Joseph Fournier—Grenoble I, Doctoral Thesis (Mar. 6, 2006).

Lenoir et al., "Volumetric Digital Image Correlation Applied to X-ray Microtomography Images from Triaxial Compression Tests on Argillaceous Rock", Strain, vol. 43 (Blackwell Publishing Ltd., 2007), pp. 193-205.

Besuelle et al., "X-Ray Micro CT for Studying Strain Localization in Clay Rocks under Triaxial Compression", Advances in X-ray tomography for Geomaterials, 2nd International Workshop on X-Ray CT for Geomaterials (2006), pp. 35-52.

Sundaram et al., "Laboratory investigations of coupled stress-deformation-hydraulic flow in a natural rock fracture", 28th US Symposium on Rock Mechanics (1987), pp. 585-592.

Li Dessau et al., "Keeping It Straight", reprint from Lasers & Optronics (1993), pp. 25-26.

Li Dessau et al., "Modular Stage Units Create Stable Custom Systems", available at http://www.newport.com/images/webDocuments-EN/images/19156.pdf.

\* cited by examiner

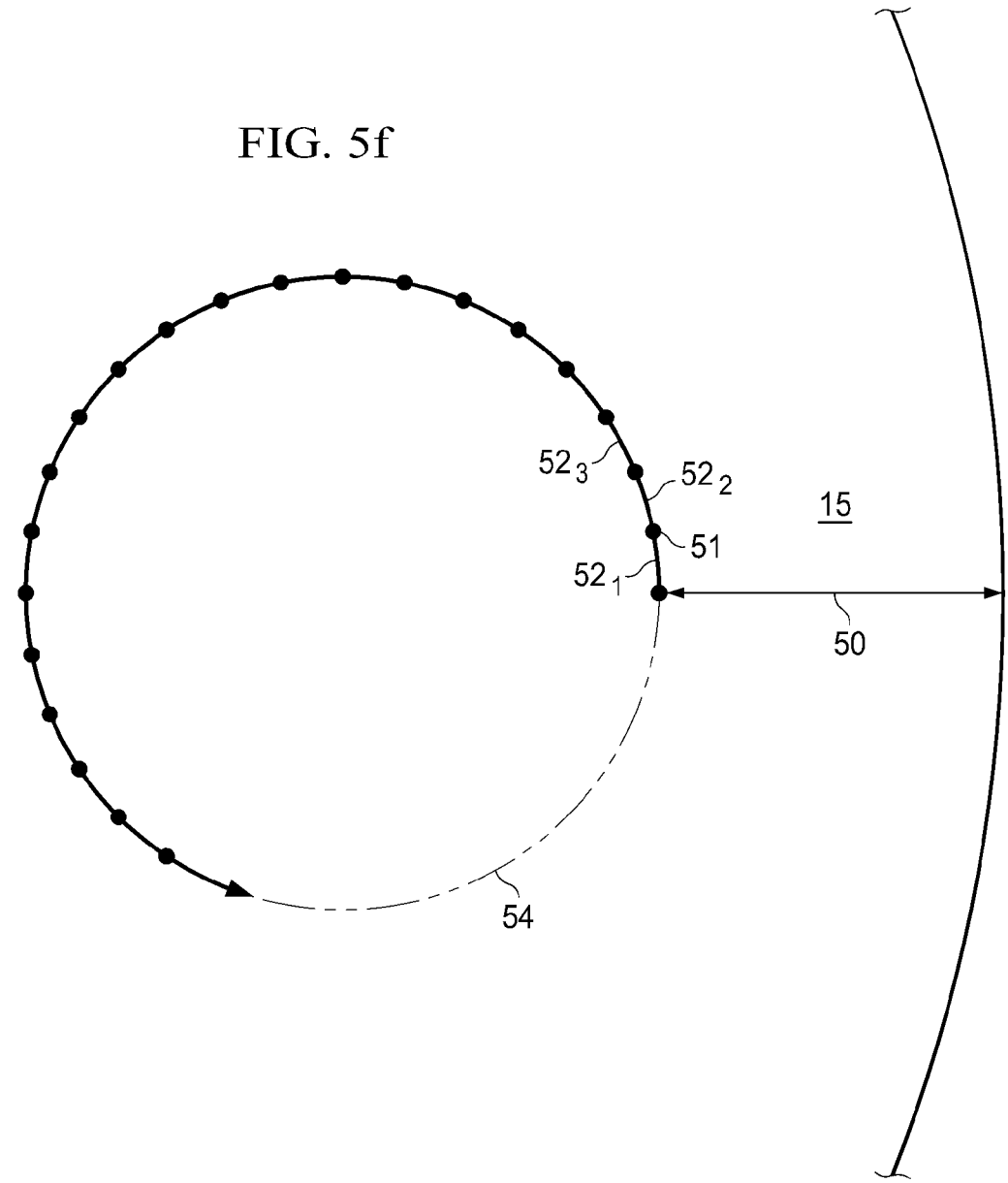

SAMPLE PREPARATION APPARATUS FOR DIRECT NUMERICAL SIMULATION OF ROCK PROPERTIES

CROSS-REFERENCE TO RELATED APPLICATIONS

This application claims priority, under 35 U.S.C. §119(e), of Provisional Application No. 61/921,797, filed Dec. 30, 2013, incorporated herein by this reference.

STATEMENT REGARDING FEDERALLY SPONSORED RESEARCH OR DEVELOPMENT

Not applicable.

BACKGROUND OF THE INVENTION

This invention is in the field of laboratory analysis of the physical properties of samples of material. Embodiments of this invention are directed to an apparatus and method for obtaining a rock sample suitable for high-resolution tomography and analysis via direct numerical simulation.

Knowledge of the properties of the material of subsurface rock formations is important for assessing hydrocarbon reservoirs in the earth and formulating a development strategy regarding those reservoirs. Traditionally, samples of the rock formation of interest are subjected to physical laboratory tests to determine these material properties, such properties also referred to as physical or petrophysical properties. However these tests are typically time consuming and expensive. For example, the measurements of certain properties of a physical rock sample require full water saturation of the sample, which can take an extremely long time if the rock has low permeability. Not only are the results not available in a timely fashion, but these tests necessarily occupy laboratory equipment over the duration of the experiment, limiting the sample throughput and thus the number of samples that can be measured in a reasonable time. It is desirable to improve the timeliness of analysis results and thus accelerate the development cycle, and also to increase the number of samples analyzed to improve the statistical confidence of the analysis results.

Direct numerical simulation of material properties from digital images of rock is a recent technology for determining the material properties of rock samples. According to this approach, an x-ray tomographic image is taken of a rock sample to produce a digital image volume representative of that sample. A computational experiment is then applied to the digital image volume to simulate the physical mechanisms from which the physical properties of the rock can be measured. Properties of the rock such as porosity, absolute permeability, relative permeability, formation factor, elastic moduli, and the like can be determined using direct numerical simulation. In particular, direct numerical simulation is capable of estimating the material properties of difficult rock types, such as tight gas sands or carbonates, within a timeframe that is substantially shorter than that required for the corresponding physical measurement. In addition, test equipment is not occupied over long periods of time according to this technique, as the analogous numerical conditions to the physical experiment can be immediately applied by the computer simulation software.

The quality of the tomographic image of the rock sample is necessarily a significant factor in the accuracy of the estimate of the material properties. X-ray tomography is based on the detection of differences in the attenuation of the incident energy by the material components (e.g., matrix space vs. pore space, or differences in rock composition). To obtain accurate estimates of the material properties, it is important that these attenuation values accurately represent the structure and material of the rock. Artifacts due to "beam hardening", or the preferential absorption of low energy photons in irregularly-shaped rock samples, degrade the accuracy of the tomographic image. More specifically, beam hardening results from the mechanisms of photoabsorption, scattering, and photoelectric effect involved that attenuate the X-rays. Because lower energy X-rays are more affected by these mechanisms than are higher energy X-rays, the beam is said to "harden" in that the mean energy of the beam increases upon passing through the sample. The shape of the sample can cause this beam hardening to vary with position within the sample. If the cross-section of the sample is regularly shaped, for example circular, post-processing of the attenuation data readily compensates for these non-uniform beam hardening effects. However, if the sample has an irregular cross-section or otherwise has a variable thickness (e.g., polygonal cross-section), this post-processing is more difficult if not impossible. If beam hardening is not properly compensated, the digital image volume may not accurately represent the material properties of the rock.

Another factor that affects tomographic image quality is the resolution of the image, namely the size of the smallest detail distinguishable by the imaging. Image resolution is controlled by characteristics of the acquisition system components and their spatial configuration relative to the sample. Cross sectional sample size impacts image resolution, as the minimum voxel size corresponds to the longest lateral dimension of the acquired image divided by the number of detector pixels representing that longest lateral dimension. Samples in which the longest lateral dimension is relatively small (e.g., 2 mm) can thus be imaged at higher image resolution, or smaller voxel size. It is also important for the image volume "field of view" to be maximized so as to cover the largest possible volume of rock under full illumination (i.e., the sample remains in the field of view of the detector at all times).

Considering all of these factors, it has been observed that cylindrical samples of rock of relatively small diameter (e.g., on the order of 2 to 3 mm) provide the optimal cross-sectional shape and size for obtaining high quality tomographic images for direct numerical simulation using modern technology. These small cylindrical samples provide a regularly shaped cross-section for which beam hardening is minimized and correctable, voxels of smaller size for improved resolution, and good field of view under full illumination.

In addition, the length of the cylindrical sample in the axial dimension has also proven to be important. It has been observed that the longest possible axial extension of the sample maximizes the volume of material that is continuously imaged by a helical image acquisition system, and also saves time in sample preparation and placement for standard (circular) image acquisition system geometries. The volume of material that is imaged should especially be maximized for the case of coarsely-grained and heterogeneous rock, to obtain an imaged volume that is statistically representative of the formation from which the sample was taken.

Considering these factors in combination, a cylindrical rock sample of small cross-section (e.g., less than 3 mm) and relatively long axial length (e.g., greater than 10 mm) is desirable for tomographic imaging for direct numerical simulation, using conventional image acquisition systems. Meeting these geometrical requirements necessitates the cutting of the sample that is to subsequently be imaged from a larger sample (e.g., a core sample, drill cuttings, etc.) that is itself obtained from the sub-surface formation of interest.

In addition to these geometric requirements, accurate direct numerical simulation requires that the integrity of the material of the sampled formation be maintained in the sample to be imaged. More specifically, the preparation of the sample should not remove granular material from the edges of the sample volume, create fractures in the grains or matrix that were not previously present, loosen grains at the sample perimeter, or otherwise deform grain shapes or pore space characteristics. This requires cleanly, directly, and non-destructively cutting through individual grains of the rock.

Conventionally, the coring of a volume of rock to obtain a small cylindrical sample suitable for imaging has been performed by drilling with a hollow drill bit, commonly referred to as a "core bit". It has been observed that this coring technique is suitable for reliably obtaining samples as small as 4 mm in diameter from some rock types. At smaller diameters, however, this approach tends to strip or fracture grains of the rock, which destroys the sample. In addition, coring in this manner has proven to be unsuitable for certain rock types, particularly rock that contains granular or sedimentary material that is not highly consolidated.

Conventional core bits also are limited in the axial length of the thin cylindrical sample that is obtained. Typically, the maximum axial length of a 3 mm core sample that can be obtained by a core bit is on the order of 5 mm. As mentioned above, it is desirable to obtain samples for imaging that are significantly longer than 5 mm, especially for use in connection with helical image acquisition systems.

Another conventional approach to the preparation of samples for tomographic imaging in the direct numerical simulation context is the cutting of rock with a diamond disc saw. This approach can obtain relatively long samples of small cross-section along the axial dimension, with minimal degradation of the sample at its cut edges. But because the disc saw is only able to cut along a two-dimensional plane, the prepared sample will have a rectangular cross-section, which results in significant loss of the imaged volume necessitated by compensation for beam hardening, given the non-uniform distances traveled by the incident energy in the sample. For example, the resulting image volume from a parallelepiped sample contains only about 60% of the voxels that can be obtained from a similarly sized cylindrical sample. Other disadvantages resulting from the parallelepiped sample shape include poor compatibility of the sample with flow or pressure cells, and the inability to perform "region of interest" (ROI) evaluations.

By way of further background, the preparation of samples for microscopy using a diamond wire saw is known in the art. One example of a conventional diamond wire saw uses a thin stainless steel wire onto which industrial diamonds of varying grit size are embedded. The cutting motion can be either reciprocating or in one direction. Examples of these conventional diamond wire saws include those available from Well Diamond Wire Saws, Inc.

BRIEF SUMMARY OF THE INVENTION

Embodiments of this invention provide an apparatus and method for obtaining cylindrical samples of rock with extremely small cross-sectional diameter for use in connection with tomographic imaging.

Embodiments of this invention provide such an apparatus and method that are capable of obtaining such samples from various rock types without significantly degrading the material integrity of the sample.

Embodiments of this invention provide such an apparatus and method that are capable of obtaining such samples from poorly consolidated rock, without requiring epoxy impregnation and similar techniques to maintain structural integrity.

Embodiments of this invention provide such an apparatus and method that is capable of obtaining samples of any one of a number of cross-sectional shapes, including those of cylindrical, rectangular, and polygonal cross-sections.

Other objects and advantages of embodiments of this invention will be apparent to those of ordinary skill in the art having reference to the following specification together with its drawings.

Embodiments of the invention may be implemented into wire cutter apparatus, comprising a table, a wire supply drum and a guiding roller that are vertically displaced from the wire supply drum and that each have an axis parallel with one another, cutting wire wound about the wire supply drum and the guiding roller, and extending from the wire supply drum around the guiding roller and back to the wire supply drum so that parallel lengths of the cutting wire extending between the wire supply drum and the guiding roller define a cutting plane, a holder for holding a specimen of material to be cut by the cutting wire, and a plurality of translation stages movable relative to the table. The plurality of translation stages comprise a feed translation stage, coupled to the holder, movable in a feed direction that is substantially parallel to the cutting plane; a first translation stage coupled to the holder that is movable in a first direction at an angle to the feed direction, and a second translation stage coupled to the holder that is movable in a second direction at an angle to the feed direction.

Embodiments of the invention may also be implemented into a method of cutting a rock sample, comprising operating a wire saw to advance a cutting wire from a wire supply drum around a guiding roller, where forward and return lengths of the cutting wire run between the wire supply drum and guiding roller and define a cutting plane, cutting a path from an edge of a specimen of rock to a starting point and then actuating either or both of first and second translation stages to linearly advance the specimen in a direction not parallel to the cutting plane. After linearly advancing the specimen in the direction not parallel to the cutting plane, the method then involves stopping the advancing of the specimen until the cutting wire substantially straightens, and repeating the actuating and stopping steps a plurality of times to cut a closed figure in the specimen defining a perimeter of the sample. The specimen may then be withdrawn along the path.

BRIEF DESCRIPTION OF THE SEVERAL VIEWS OF THE DRAWING

FIG. 5f is a schematic plan view of the perimeter of a sample cut from a larger specimen, at a stage of the method of FIG. 4 according to that embodiment of the invention.

DETAILED DESCRIPTION OF THE INVENTION

Figure 1:
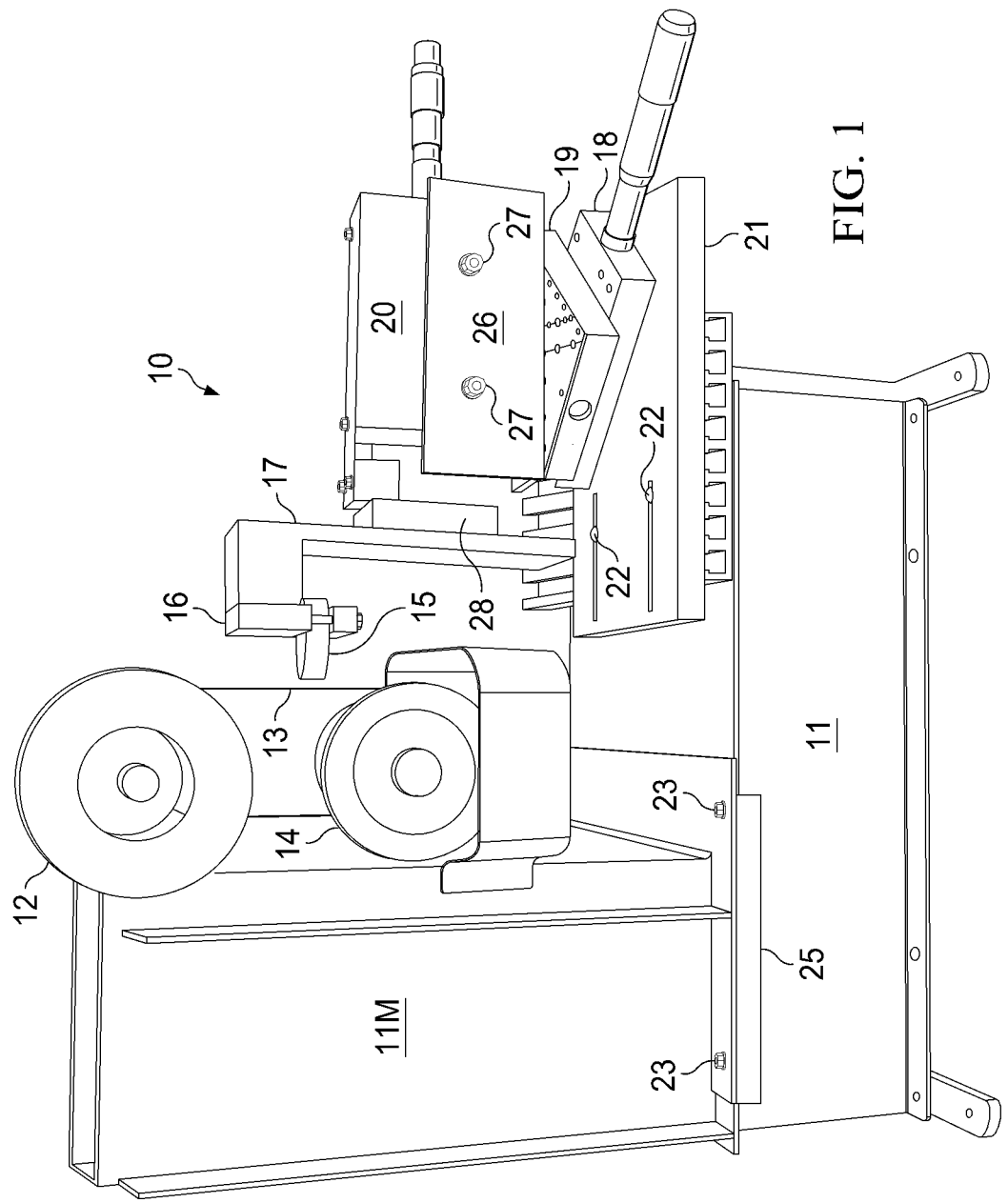
FIG. 1 is an elevation view of a sample preparation apparatus constructed according to an embodiment of the invention.

This invention will be described in connection with its embodiments, namely as implemented into an apparatus and method of preparing a rock sample for use in digital numerical simulation analysis of the properties of the rock from which that sample was acquired, as it is contemplated that this invention will be especially beneficial in such an application. However, it is contemplated that this invention will be useful and beneficial in other applications beyond those described in this specification. Accordingly, it is to be understood that the following description is provided by way of example only, and is not intended to limit the true scope of this invention as claimed.

As discussed above in connection with the Background of the Invention, embodiments of this invention pertain to the acquiring of rock samples and their analysis by way of direct numerical simulation. As such, it is contemplated that embodiments of this invention will be especially beneficial in the acquiring of rock samples from sub-surface formations important in the exploration and production of oil and gas. More specifically, the rock from which these samples will be acquired are contemplated to correspond to formations accessed by terrestrial or marine drilling systems such as used to extract resources such as hydrocarbons (oil, natural gas, etc.), water, and the like from those formations. As is fundamental in the art, the optimization of oil and gas production operations is largely influenced by the structure and physical properties of these sub-surface rock formations. The samples obtained according to embodiments of this invention are useful in understanding those formation attributes.

As will be evident from the following description, embodiments of this invention are more specifically directed to the obtaining of small samples of rock from larger samples of the rock of interest that were previously recovered from the sub-surface. For the sake of clarity, those larger samples of rock will be referred to as "specimens" in this description, and the small samples of rock obtained from those specimens will be referred to as "samples". No particular connotation is intended by the separate terms "specimens" and "samples"; rather, the use of these separate terms is merely intended to distinguish the small samples obtained according to this invention from the larger samples from which those small samples are obtained.

Conventional diamond wire cutters are used for the preparation of samples, including samples of rock that are obtained for petrophysical property analysis. An example of such a conventional diamond wire cutter is the 3242 Diamond Wire Cutter available from Well Diamond Wire Saws, Inc. However, it has been observed, in connection with this invention, that conventional wire cutters such as that 3242 Diamond Wire Cutter are not readily capable of cutting in a curved path as is necessary for the preparation of cylindrical samples, particularly those with a small (<10 mm) cross-sectional diameter. One reason for this limitation is that the arrangement of the cutting wire in these conventional cutters, generally running vertically between a wire supply drum and a guiding roller, do not allow shear forces to be applied to the cutting wire. In such conventional wire cutters, these shear forces can cause the cutting wire to become stuck in the workpiece, or to become dislodged from the guiding roller. In addition, because the diamond cutting wire bends during cutting, with a curvature corresponding to the applied force and also the working length of the workpiece material, an even cut can only be obtained in one direction, namely the feed direction. These conventional diamond wire cutters such as the 3242 Diamond Wire Cutter also provide only a single degree of freedom in the movement of the cutting wire relative to the workpiece. For example, the 3242 Diamond Wire Cutter maintains a fixed position of the workpiece, with the only permitted movement being the movement of the cutting wire toward and away from the workpiece. This single degree of freedom provided by this conventional diamond wire cutter necessitates a unidirectional cut.

FIG. 1 illustrates the construction of sample preparation apparatus 10 according to an embodiment of this invention. As will become apparent from the following description, sample preparation apparatus 10 is capable of obtaining small samples of the desired cross-section, typically circular but also other shapes such as polygons, from a larger specimen of the rock of interest. It is contemplated that the manner in which the rock specimens are obtained from the sub-surface, and the physical form of those specimens, can vary widely. Examples of rock specimens useful in connection with embodiments of this invention include whole core samples, side wall core samples, outcrop samples, drill cuttings, and laboratory generated synthetic rock samples such as sand packs and cemented packs.

In this embodiment of the invention shown in FIG. 1, sample preparation apparatus 10 includes table 11, which provides a stable base for the other components of apparatus 10. Wire supply drum 12 is mounted to table 11 via its motor enclosure 11M, and is motor-driven to rotate about its axis. In this embodiment, guiding roller 14 is mounted to table 11 at a vertical position below wire supply drum 12, with its axis parallel to that of wire supply drum 12. Diamond cutting wire 13 is wound about wire supply drum 12, around guiding roller 14, and back to wire supply drum 12 as shown. The vertical position of guiding roller 14 relative to wire supply drum 12 may be adjustable, providing a tensioning device to maintain the desired tautness in cutting wire 13. Cutting wire 13 of conventional construction, for example a diamond-impregnated wire of about 60 µm grit and about 300 µm in diameter, is suitable for sample preparation of typical rocks of interest; of course the grit and diameter of cutting wire can vary according to the sample materials.

Table 11, wire supply drum 12, and guiding roller 14 in apparatus 10 are similar components as provided in conventional diamond wire cutters, such as the 3242 Diamond Wire Cutter. According to embodiments of this invention, motor enclosure 11M may be unitary with table 11, or alternatively may be a separate module that is attached to table 11. In the conventional operation of the 3242 Diamond Wire Cutter, its motor enclosure moves, relative to its table, to advance the cutting wire to the specimen. However, according to embodiments of this invention, if motor enclosure 11M is a separate module, motor enclosure 11M is mounted to table 11 in a fixed position by cap screws 23 and bracket 25 as shown in FIG. 1; another pair of cap screws 23 and another bracket 25 are also present on the other side of motor enclosure 11M in that FIG. 1. Because motor enclosure 11M is in a fixed position relative to table 11, wire supply drum 12 and guiding roller 14, and thus cutting wire 13, are also in a fixed position relative to table 11.

Conversely, according to embodiments of this invention, apparatus 10 is constructed so that the workpiece, namely specimen 15 of FIG. 1 from which the rock sample is to be cut, is movable in multiple degrees of freedom relative to cutting wire 13, which is maintained at a fixed position. In apparatus 10 shown in FIG. 1, the position of positioning table 21 on table 11 can be adjusted along tracks in positioning table 21, and then fixed in position by fixing screws 22. In any case, it is contemplated that, once adjusted and set, positioning table 21 will remain fixed in position relative to table 11 during sample preparation.

According to this embodiment of the invention, three linear translation stages 18, 19, 20 are coupled to positioning plate 21. More specifically, linear translation stages 18, 19, 20 in this example are modular positioning stages, mounted in a stacked manner relative to one another. As shown in FIG. 1 generally, and in more detail in FIG. 2, y-translation stage 18 is mounted to positioning table 21, x-translation stage 19 is mounted to y-translation stage 18, and f-translation stage 20 is mounted to x-translation stage 19.

Figure 2:
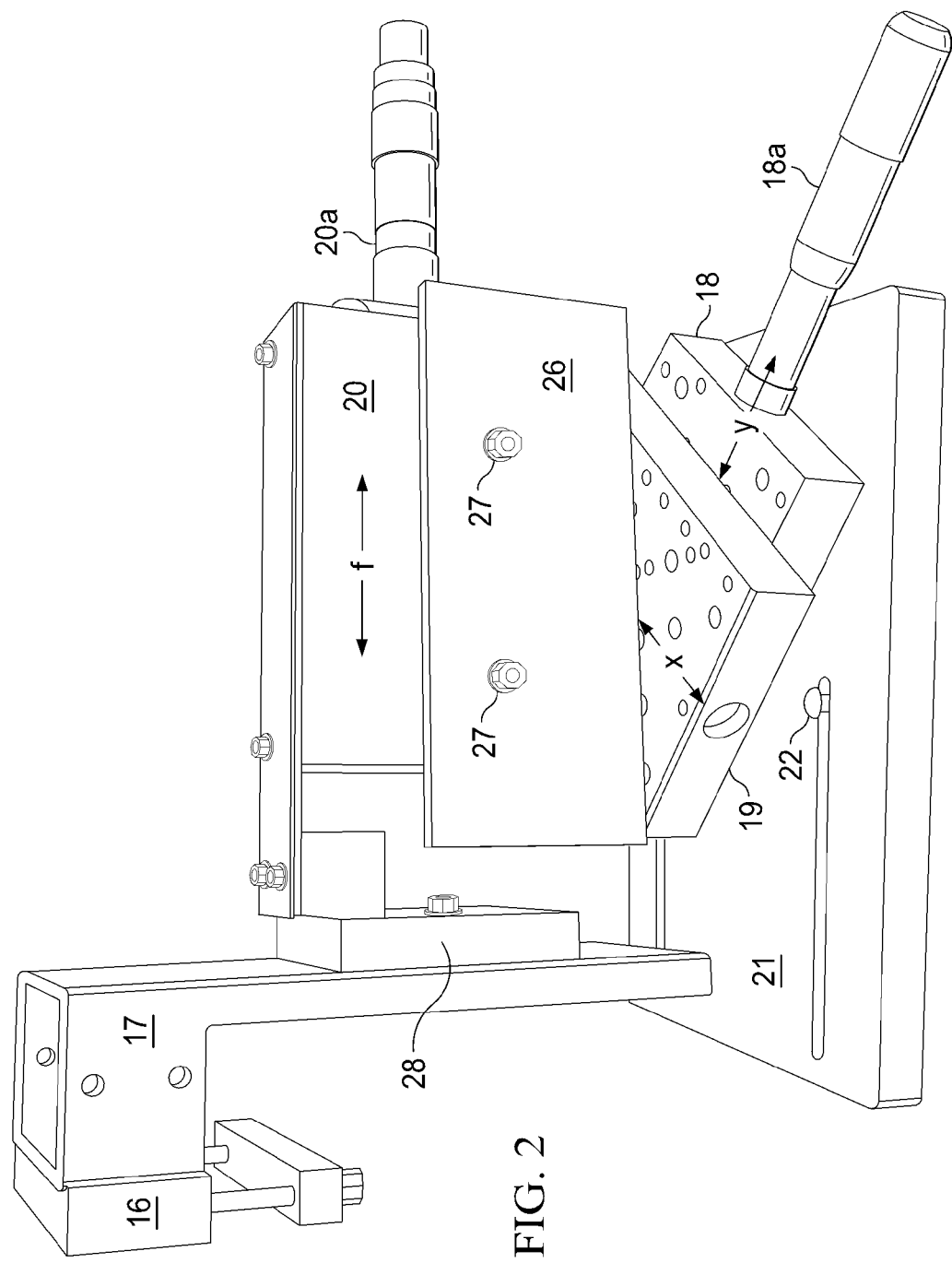
FIG. 2 is a perspective view of the translation stages and specimen holder of the apparatus of FIG. 1, according to that embodiment of the invention.
Figure 3:
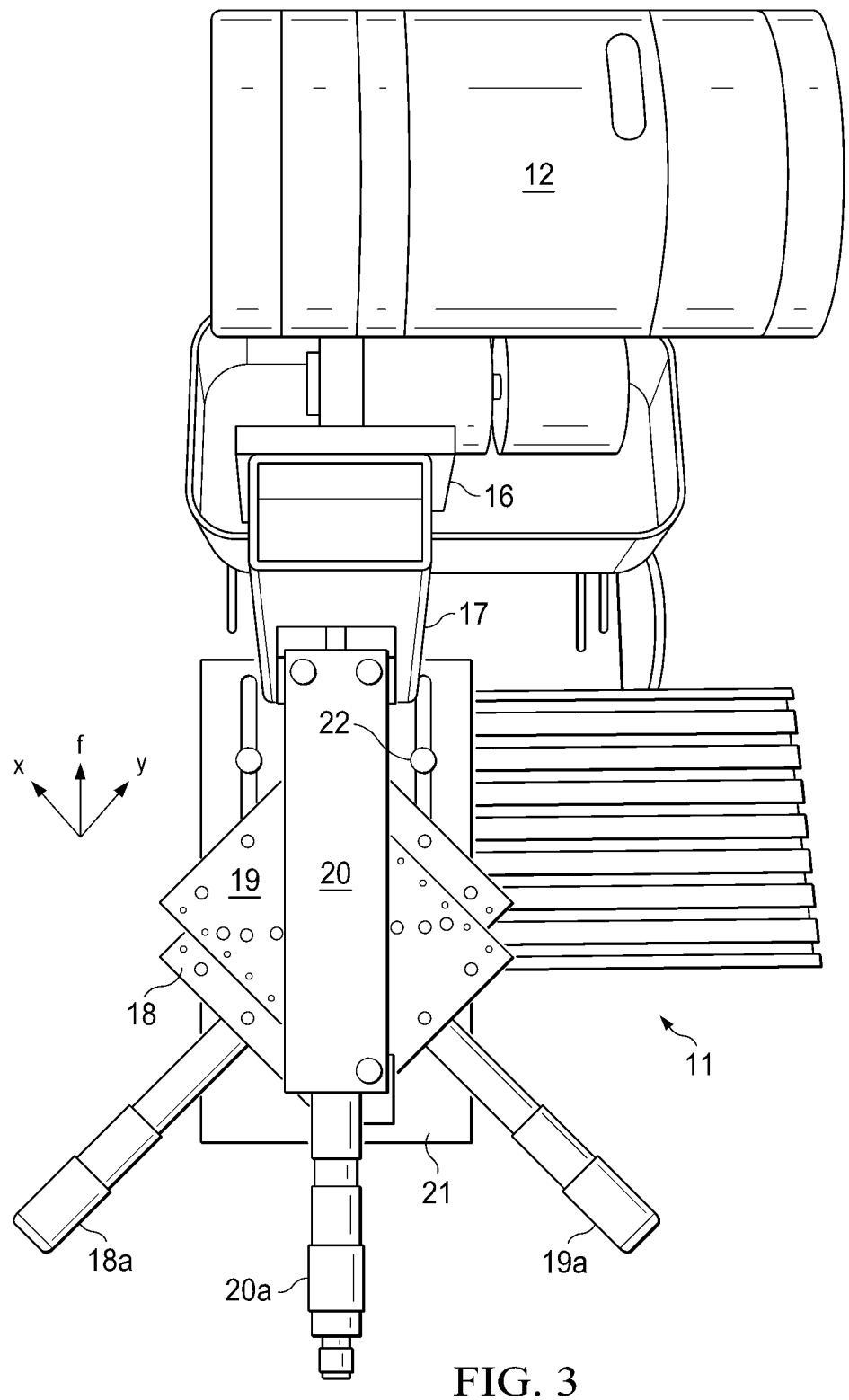
FIG. 3 a plan view of the sample preparation apparatus constructed according to that embodiment of the invention.

Translation stages 18, 19, 20 in this embodiment of the invention are conventional linear translation stages as known in the art. For example, each of translation stages 18, 19, 20 may be constructed to have a stage body that is mountable (e.g., by way of bolts) to a fixed plate, and a carriage that is movable in a single direction along a track or rail under the control of an actuator. FIGS. 2 and 3 illustrate micrometer actuators 18a, 19a, 20a coupled to translation stages 18, 19, 20, respectively. The directions of travel provided by each of translations stages 18, 19, 20 is indicated in FIGS. 2 and 3 by the "y", "x", and "f" arrows, respectively. An example of a suitable linear translation stage suitable for use as translation stages 18, 19, 20 is the M-UMR 8.51 manual translation stage, with the BM17.51 micrometer actuator, as available from Newport Spectra-Physics, Ltd.

For the example of modular translation stages 18, 19, 20 as shown in FIGS. 1 and 2, and as mentioned above, the stage body of y-translation stage 18 is fixed by way of bolts or the like to positioning plate 21, such that movement of its carriage relative to its stage body, and thus relative to positioning plate 21, will be along the y-direction as shown in FIG. 2. In this example, the stage body of x-translation stage 19 is fixed by way of bolts or the like to the carriage of y-translation stage 18, such that movement of its carriage relative to its stage body, and thus relative to the carriage of y-translation stage 18, will be along the x-direction shown in FIG. 2. In this example, L-shaped plate 26 is mounted to the carriage of x-translation stage 19, and the stage body of f-translation stage 20 is mounted to plate 26 by way of bolts 27, such that f-translation stage 20 is mounted perpendicularly to translation stages 18, 19. Movement of the carriage of f-translation stage 20 relative to its stage body, and thus relative to the carriage of x-translation stage 19, will be along the f-direction shown in FIG. 2.

In this embodiment, as described above and as will be described below, guiding roller 14 is vertically displaced relative to wire supply drum 12, so that the paths of cutting wire 13 between wire supply drum 12 and guiding roller 14 are substantially vertical; in this arrangement, the directions of travel of x-translation stage 19, y-translation stage 18, and f-translation stage 20 are all in a horizontal plane that is orthogonal to the cutting plane defined by the vertical paths of cutting wire 13. It is contemplated, however, that guiding roller 14 may be displaced in a direction other than vertical relative to wire supply drum 12. For example, guiding roller 14 may be mounted so that the paths of cutting wire 13 travel in a horizontal path. In that case, x-translation stage 19, y-translation stage 18, and f-translation stage 20 would be rotated accordingly, so that their respective directions of travel would be in a vertical plane that is orthogonal to the horizontal plane. Of course, orientations other than the vertical and horizontal are also contemplated in connection with this embodiment.

It is contemplated that other types of translation stages, including integrated translation stages replacing two or more of modular translation stages 18, 19, 20 may alternatively be used. Alternatively, one or more of translation stages 18, 19, 20 may be provided with a motorized actuator instead of the micrometer actuators 18a, 20a as shown. According to this alternative approach in which actuators 18a, 19a, 20a are motorized, it is contemplated that sample preparation apparatus 10 may also include, if desired, a computer or other programmable controller capable of controlling these actuators 18a, 19a, 20a according to a pre-programmed sequence, so as to automate the cutting of a sample from specimen 15 in a consistent and repeatable manner. In this embodiment, x-translation stage 19 and y-translation stage 18 are orthogonal to one another, and as such have carriages that are movable in directions that are substantially perpendicular to one another, as it is believed that such an arrangement will facilitate efficient control, it is further contemplated that these translation stages may alternatively be oriented at an angle other than perpendicular to one another if desired.

In this embodiment of the invention, specimen 15 (shown in FIG. 1) is held by specimen holder 16, which is mounted to f-translation stage 20 by way of vertical adjustment plate 17 and bracket arrangement 28. Specimen holder 16 is contemplated to include jaws or another type of clamping arrangement for securely holding specimen 15 during the cutting process. Vertical adjustment plate 17 allows adjustment of the vertical position of specimen holder 16, and thus specimen 15. In this embodiment of the invention, the fixed coupling of specimen holder 16 to f-translation stage 20, and the stacked arrangement of translation stags 18, 19, 20, allows a translation by one or more of translation stages 18, 19, 20 to effect movement of specimen 15 in the corresponding directions.

As shown in the plan view of FIG. 3 in combination with FIGS. 1 and 2, the f-direction of translation by f-translation stage 20 is contemplated to be substantially parallel to a cutting plane defined by the two paths followed by cutting wire 13 that extends from wire supply drum 12 around guiding roller 14 and back. According to embodiments of the invention, as will be described in further detail below, translation of specimen 15 along the f-direction is used for advancing specimen 15 toward wire 13, and for withdrawing specimen 15 from wire 13. During the remainder of the cutting process, particularly in the cutting of a closed figure to define the sample being cut from specimen 15, translation of specimen 15 will be controlled by x-translation stage 19 and y-translation stage 18.

According to this embodiment of the invention, apparatus 10 provides degrees of freedom, in the x and y directions, that enable the cutting of samples of varying and arbitrary cross-sectional shape from rock specimens. And as will be described in detail below, the operation of apparatus 10 according to embodiments of the invention enable the cutting of samples of very small cross-sectional diameter, thus reducing voxel size within the imaged volume, which improves the accuracy of the material property estimates derived via direct numerical simulation.

Figure 4:
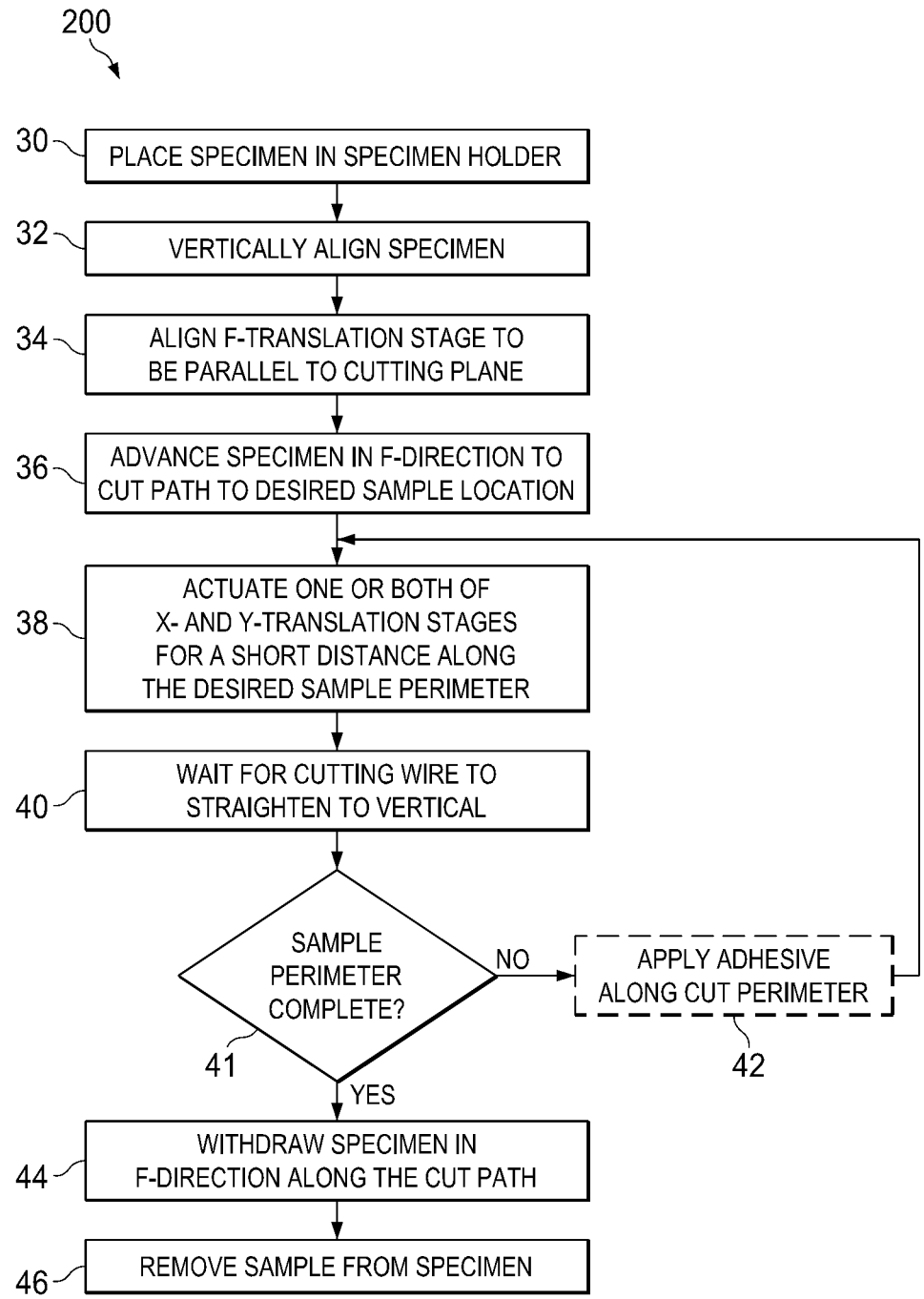
FIG. 4 is a flow diagram illustrating a method of preparing a sample according to an embodiment of the invention.

Referring now to FIG. 4 in combination with the schematic diagrams of FIGS. 5a through 5e, the operation of apparatus 10 in preparing a sample from a specimen of rock according to embodiments of this invention will now be described. As described above, specimen 15 may be acquired in any one of a number of conventional ways. In the context of the oil and gas industry, specimen 15 will typically be derived from the drilling of exploration or production wells, and as such may come from whole core samples, side wall core samples, outcrop samples, and drill cuttings; alternatively, specimen 15 may be produced from a laboratory generated synthetic rock sample such as a sand pack or a cemented pack. According to embodiments of this invention, the nature of the rock from which specimen 15 consists can be quite wide ranging, including less consolidated and structurally robust materials such as sandstones, clays, and other granular or sedimentary material that is not highly consolidated.

Figure 5A:
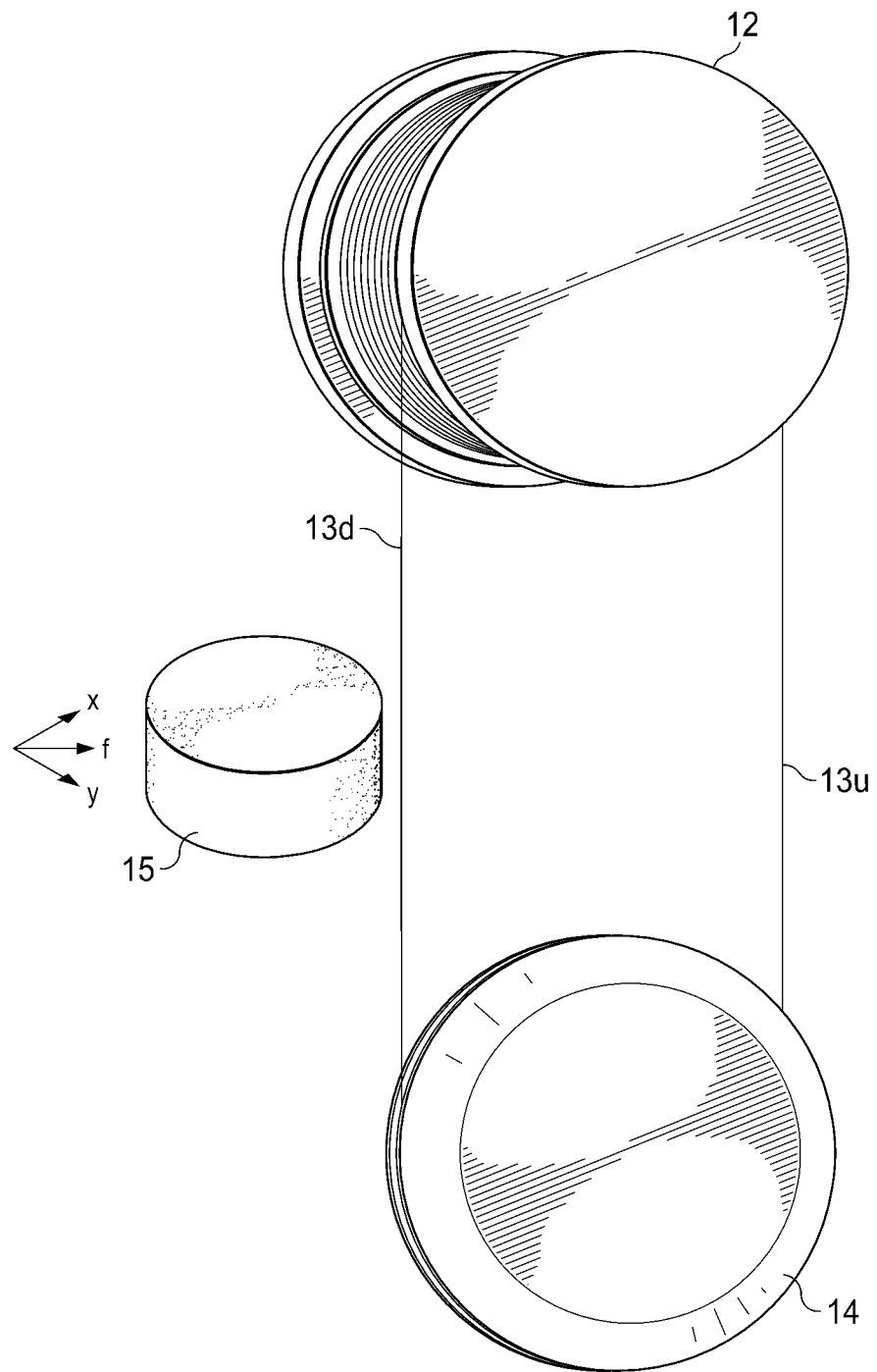
FIGS. 5a through 5e are schematic views of a specimen and the cutting wire subsystem of the apparatus of FIG. 1, at various stages of the method of FIG. 4, according to that embodiment of the invention.

Sample preparation process 200 begins, in this embodiment of the invention, with process 30 in which specimen 15 is placed into and retained by specimen holder 16. For the example in which specimen holder 16 includes a pair of jaws, process 30 consists of the fixing of specimen 15 in those jaws. In many cases, a cylindrical sample is desired to be cut from specimen 15, in which case it is desirable for specimen 15 to have flat top and bottom surfaces, and have a thickness corresponding to the desired length of the sample to be recovered. As shown in FIG. 5a, specimen 15 may have a cylindrical shape (i.e., disk-shaped), as typical for prepared core samples obtained from the drilling process.

Once placed in specimen holder 16, sample 15 is positioned and oriented at the desired location of cutting wire 13 in process 32, as shown in FIG. 5a. The vertical position of specimen 15 is adjusted by way of vertical adjustment plate 17. For the case of a disk-shaped specimen 15, its flat surfaces will be optimally oriented to be perpendicular to cutting wire 13, to produce a cylindrical sample. In process 34, f-translation stage 20 is aligned so that its movement will be parallel to the cutting plane defined by cutting wire 13. Referring to FIG. 5a, cutting wire 13 is shown as having two vertical lengths $13d$, $13u$, extending from wire supply drum 12 around guiding roller 14 vertically displaced beneath wire supply drum 12, and back again, with the vertical lengths $13d$, $13u$ being substantially parallel to one another, defining a plane referred to in this description as the cutting plane. In this example, motor 11M operates so that the cutting motion of cutting wire 13 is reciprocal, as is typical for wire saws. Alternatively, roller 14 may be replaced by a second wire supply drum if desired. In the example of apparatus 10 described above, the alignment of f-translation stage 20 in process 34 is contemplated to be accomplished by moving positioning plate 21 (to which translation stages 18, 19, 20 are mounted) relative to table 11, and fixing positioning plate 21 in place by tightening fixing screws 22. Proper alignment of f-translation stage 20 so that translation is parallel to the cutting plane ensures that specimen 15 may be cut into for the desired length without imparting shear forces on wire length $13d$. Alignment process 34 optimally places specimen 15 as close to wire length $13d$ as practicable, so that much of the travel limit of f-translation stage 20 will be within specimen 15; it is also useful for actuators $18a$, $19a$ of translation stages 18, 19, respectively, to be initially set at their medial values so that each can exert the maximum travel in either direction.

Figure 5B:
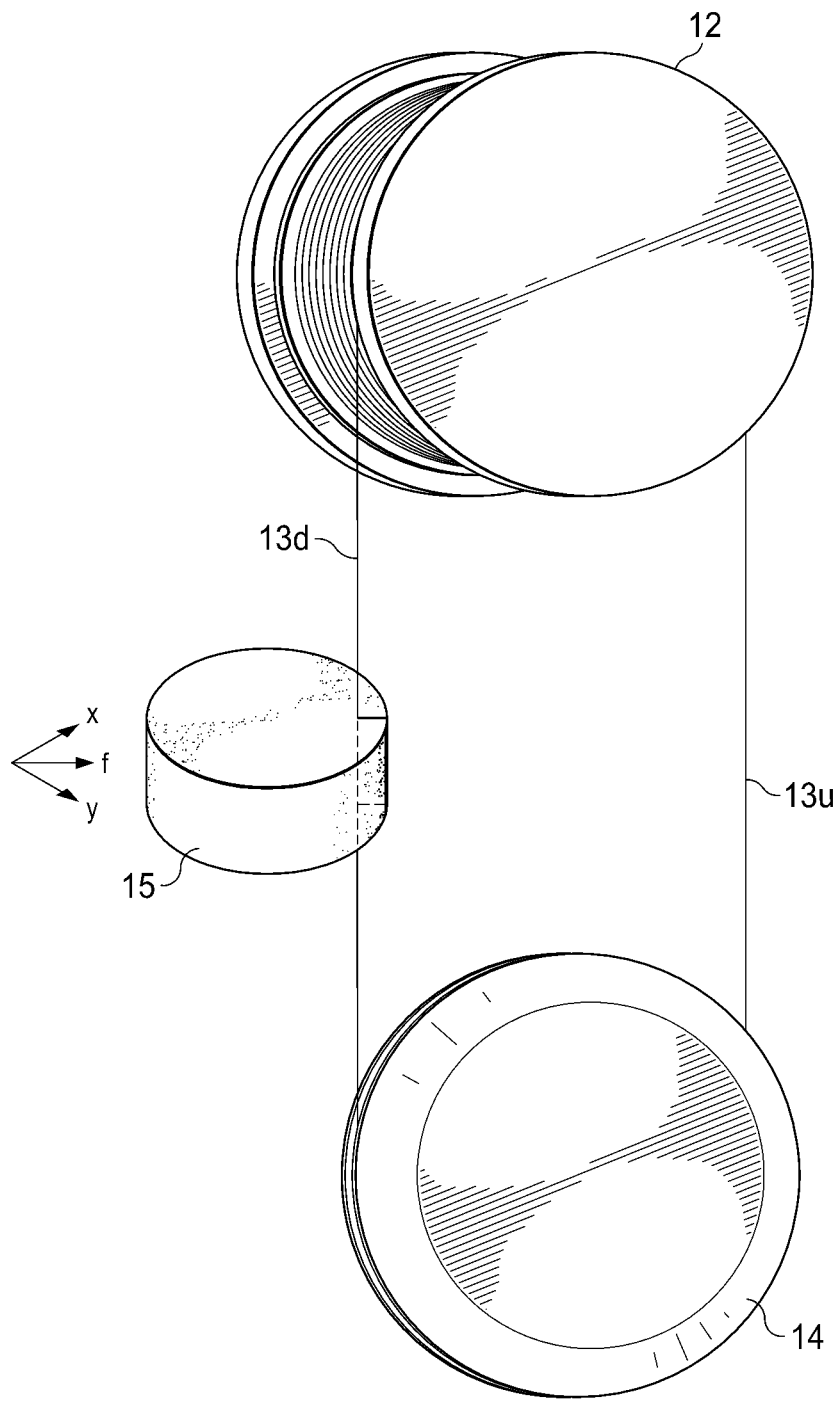

In process 36, f-translation stage 20 is actuated (via actuator $20a$) to advance specimen 15 toward and against cutting wire length $13d$. This translation of specimen 15, in the f-direction only, bends wire length $13d$ as shown in FIG. 5b, but this bending is in the cutting plane defined by wire lengths $13d$, $13u$, and as such imparts minimal shear forces on cutting wire 13. As such, the cutting of process 36 may be performed "non-stop" if desired. In any case, process 36 continues until a path of the desired length is cut into specimen 15. More specifically, it is contemplated that this path will extend from the perimeter of specimen 15 up to the point within specimen 15 at which the perimeter of the sample to be cut will begin.

Following process 36, the cutting of the perimeter of a sample from specimen 15 begins in process 38, with the actuation of one or both of actuators $18a$, $19a$ to move either or both of x- and y-translation stages 18, 19, respectively, and thus specimen 15 for a short distance according to the desired sample perimeter. According to embodiments of this invention, the resulting translation by either or both of x- and y-translation stages 18, 19 will generally be out of the f-direction cutting plane defined by wire lengths $13d$, $13u$, and as such shear forces will be applied against wire length $13d$. However, the effect of these shear forces is minimized by limiting the distance and rate at which specimen 15 is moved in process 38. For example, the distance of the translation in process 38 is very short, for example no more than about 100 μm for the example of apparatus 10 based on the Model 3242 Diamond Wire Cutter referenced above. The feed rate of cutting wire 13 from wire supply drum 12 will depend on a number of factors, including the composition of specimen 15, the thickness of cutting wire 13, the translation distance for each movement of specimen 15, and the like. For example, cutting wire 13 of a diameter of about 100 μm may be fed at a rate up to about 50 μm/sec, to cut a sandstone specimen 15. Thicker cutting wire 13 may allow a higher maximum feed rate. In any case, it is contemplated that those skilled in the art having reference to this specification will be readily able to determine a suitable feed rate and cutting wire type and diameter. These constraints of maximum translation distance and maximum wire feed rate will limit the curvature of wire length $13d$ from the vertical, and thus limit the shear forces.

After the short translation of process 38, movement of specimen 15 is ceased in process 40 for at least a minimum length of time to allow cutting wire length $13d$ to return to a straight orientation. During this wait time of process 40, cutting wire length $13d$ acts to remove material from specimen 15 along the length of the translation of process 38, straightening out as it does so, which in this arrangement results in cutting wire length $13d$ returning to the vertical. It is contemplated that the wait time of process 40 for cutting wire length $13d$ to become substantially straight will be on the order of at least about 3 seconds ranging up to about 5 seconds, for most rock materials of interest in the oil and gas context. If specimen 15 has been impregnated with epoxy to reduce damage, as is conventionally done for medium to poorly consolidated samples, this wait time may be much longer, for example as long as several minutes. It has been observed that waiting process 40 is not only beneficial to maintain the health of cutting wire 13, but also results in a straight cut throughout the depth of specimen 15, and thus good control the shape of the sample that will eventually be removed. At the end of this wait time, the combination of translation process 38 and wait process 40 will have resulted in the cutting of a short linear distance in specimen 15.

In decision 41, the user determines whether the perimeter of the sample being cut from specimen 15 is complete, in that the most recent linear cut has completed a closed figure within specimen 15. If not (decision 41 is "no"), process 38 is repeated by the actuation of either or both of x-translation stage 18 and y-translation stage 19 for a short distance. For the cutting of an approximated circle in specimen 15, the direction of each successive translation process 48 will be in a different direction from the previous. Alternatively, apparatus 10 and its operation according to embodiments of the invention can also be used to cut a polygonal cross-section, in which case the translation of a next instance of process 38 may be in the same direction as the previous. Waiting process 40 is then performed again to allow wire length $13d$ to make the cut and remove the material, straightening so as to return to the vertical. These processes 38, 40 are then repeated until it is determined, in decision 41, that the full perimeter of the sample has been cut.

Figure 5C:
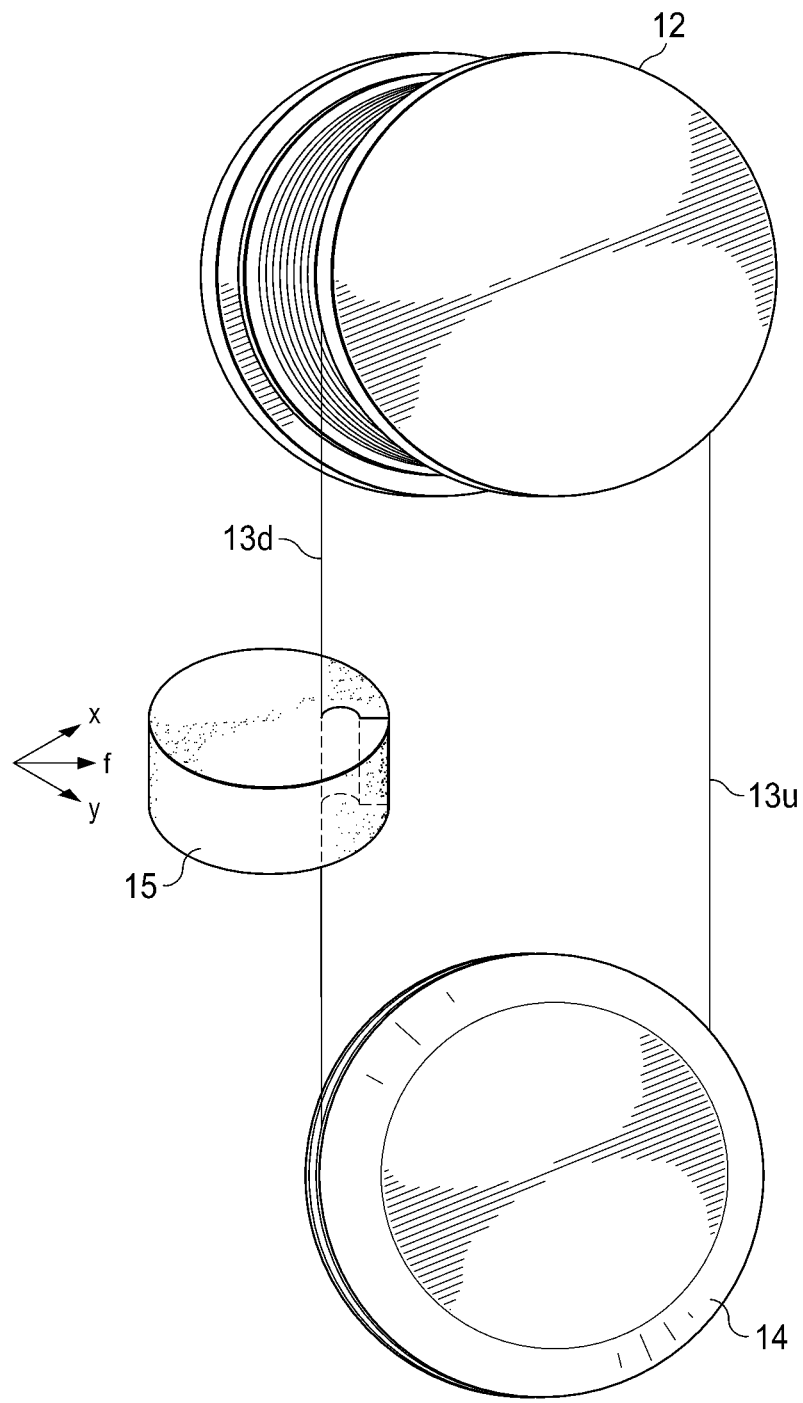

FIG. 5c schematically illustrates specimen 15 after a number of piecewise linear cuts resulting from repeated processes 38, 40, according to an embodiment of the invention. At the stage of the process shown in FIG. 5c, a portion of a circular cross-section has been defined by cutting wire 13. FIG. 5f illustrates, in plan view, this partial cutting of the sample in further detail. As shown in FIG. 5f, path 50 was cut, in process 36, from the outer surface of specimen 15 to point 51. The small linear cuts of processes 38, 40 began from point 51 with cut $52_1$, and repeated to form cuts $52_2$, $52_3$, and so on in a counter-clockwise direction in this example. (The endpoints of each cut 52 are emphasized for purposes of this explanation, but will not in fact be present in specimen 15.)

As shown in FIG. 4, optional adhesive process 42 may be performed, if desired, at one or more points during the repeated linear cuts formed by processes 38, 40. In process 42, an adhesive is applied along part of the perimeter of the sample already cut, for example after about three-fourths of the perimeter has been cut, to keep the sample from falling out upon completion of the cut. The presence of this adhesive applied in process 42 also ensures that the sample is fully cut from specimen 15, rather than prematurely breaking off from specimen 15 as the perimeter cut is nearing completion.

Figure 5D:
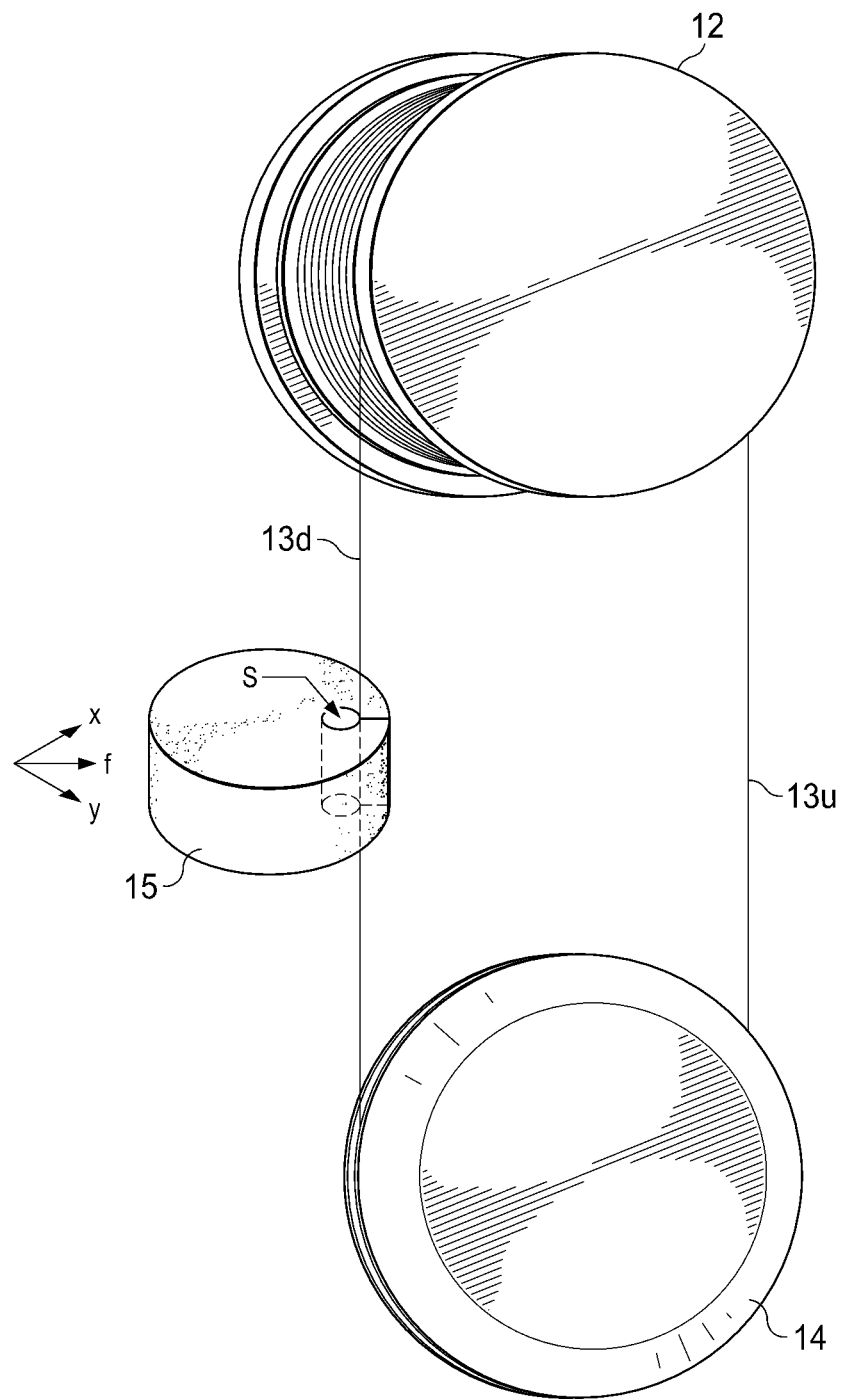

According to embodiments of this invention, the repeated processes 38, 40 continue to form cuts 52 in the same manner until forming a closed figure upon returning to point 51, as determined by decision 41. This stage of the process is illustrated in FIG. 5d, with sample S having a perimeter defined by the closed figure formed by the sequence of linear cuts 52. In this example, because each of cuts 52 is quite short, for example no longer than about 100 µm, the sequence of cuts 52 is a good approximation of circle 54, which yields a cylindrical sample from disk-shaped specimen 15. For example, it is contemplated that on the order of 60 cuts of 100 µm will cut a circle of about 2 mm in diameter, which is very useful in the context of tomography and digital numerical simulation.

Upon completion of the repeated linear cuts by processes 38, 40 (decision 41 returning a "yes" result), translation in the x- and y-directions ceases. In the example of FIG. 5f, wire length 13d is at point 51 at this point. Process 44 is then performed to withdraw specimen 15 (with sample S) from cutting wire 13, by actuating f-translation stage 20 in the direction parallel to the cutting plane (in the opposite direction from that of process 36). It is contemplated that little or no additional cutting of specimen 15 will typically take place in process 44.

Figure 5E:
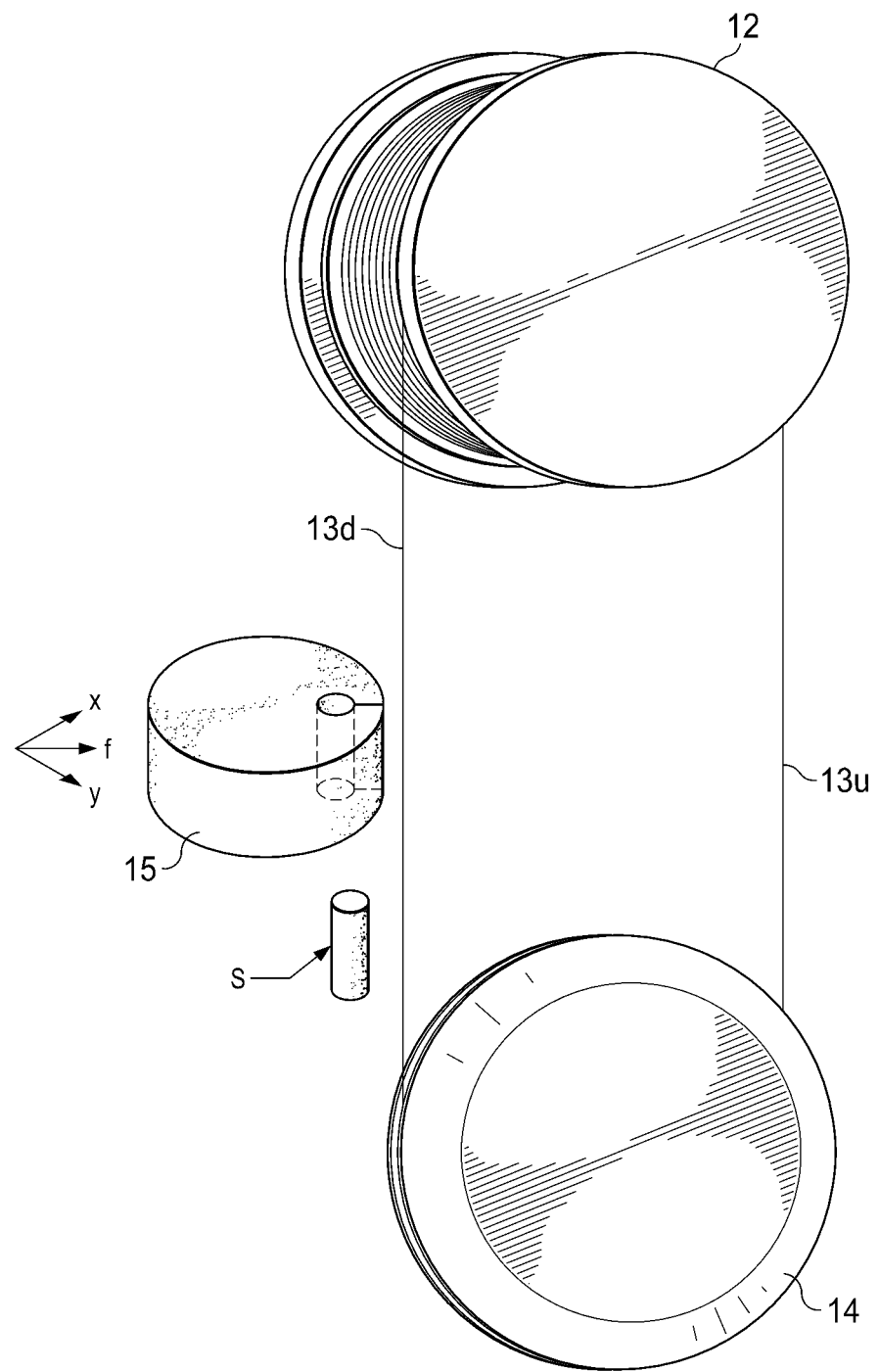

Following process 44, sample S is then removed from specimen 15, for example by removing the adhesive applied in process 42 if present, or by otherwise pushing sample S from specimen 15, in process 46. FIG. 5e schematically illustrates the removal of sample S from specimen 15, following withdrawal of specimen 15 from cutting wire length 13d in process 44. Specimen 15 may be removed from specimen holder 16 either prior to, or after, removal process 46. Alternatively, specimen 15 may be repositioned in specimen holder 16 (with sample S retained in specimen 15 by adhesive, if desired), and sample preparation process 200 repeated, if another sample is to be cut from this same specimen 15.

According to the embodiment of the invention described above, in which specimen 15 is advanced by f-translation stage 20 in process 36 in the f-direction parallel to the cutting plane of wire lengths 13d, 13u, the overall cutting time can be minimized as the cutting of specimen 15 from its edge to starting point 51 can be done continuously, without stopping. Alternatively, specimen 15 may be cut from its edge to starting point 51 along a path running in directions that are not parallel to the cutting plane, by way of a series of short piecewise linear cuts carried out by translations in the x- and y-directions by translation stages 18, 19, separated by wait times, such as performed in processes 38 and 40 to cut the perimeter of the sample. This non-parallel approach may be useful for particular sample geometries, or if specific portions of specimen 15 are to be avoided.

As mentioned above, sample preparation apparatus 10 may be constructed to include a computer or other programmable controller that controls the sequence in which actuators 18a, 19a, 20a operate to move specimen 15. This automated approach to sample preparation can be particularly useful in ensuring that the appropriate wait time following one of the piecewise cuts elapses before initiating the next cut. In connection with this automated implementation, it is further contemplated that sensors may also be implemented into sample preparation apparatus 10, for example to sense the time at which wire 13d returns to the vertical following translation of specimen 15, following which the translation of specimen 15 in the direction of a next cut can then begin.

Figure 6:
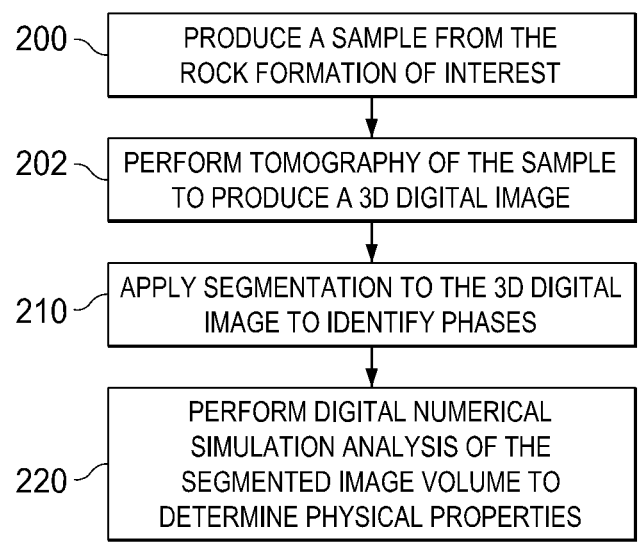
FIG. 6 is a flow diagram illustrating a method of analysis of a rock sample according to an embodiment of the invention.

Referring now to FIG. 6, the overall process of the estimation of material properties using digital numerical simulation, from samples prepared according to embodiments of this invention, will be described. The estimation process begins with sample preparation process 200, carried out in the manner described above relative to FIGS. 4 and 5a through 5f according to embodiments of this invention to produce one or more rock samples for imaging.

In process 202, an imaging system obtains two-dimensional (2D) or three-dimensional (3D) images, or other appropriate image representations, of the rock sample prepared in process 200. These images and representations obtained in process 202 include details of the internal structure of the samples. An example of the imaging device used in process 202 is an X-ray computed tomography (CT) scanner, of a type, construction, or other attributes corresponding to any one of a number of x-ray devices capable of producing an image representative of the internal structure of the sample of the desired resolution. For example, a plurality of two-dimensional (2D) sectional images of the sample may be acquired, and forwarded to a computing device that then constructs a three-dimensional (3D) digital image volume corresponding to the sample. Conventional computing devices suitable for performing this construction and the subsequent analysis may be any one of a number of conventional computers, for example, a desktop computer or workstation, a laptop computer, a server computer, a tablet computer, and the like, having sufficient computational capacity to carry out the desired operations.

Specific conventional techniques for acquiring and processing 3D digital image volumes of the sample in process 202 include, without limitation, X-ray tomography, X-ray micro-tomography, X-ray nano-tomography, Focused Ion Beam Scanning Electron Microscopy, and Nuclear Magnetic Resonance.

This image volume is typically represented by 3D regular elements called volume elements, or more commonly "voxels", each having an associated numeric value, or amplitude, that represents the relative material properties of the imaged sample at that location of the represented medium. In process 210, the computing device performs segmentation or other image enhancement techniques on the digital image volume of the sample to distinguish and label different components in the image volume. For example, segmentation process 210 may identify the significant elastic components, such as pore space and mineralogical components (e.g., clays and quartz), that can affect the elastic characteristics of the sample. Segmentation process 210 may be performed to identify more than two significant elastic phases, representing such material constituents as pore space, clay fraction, grain contacts, and individual grains and minerals. The particular segmentation algorithm used by the computing device in process 210 may vary according to the analysis desired; typically some type of "thresholding" is applied, to group voxels having similar amplitudes with one another. Conventional image processing to enhance the image volume, to reduce noise, etc. may be included in process 210 as known in the art.

In process 220, a computing device then performs digital numerical simulation to analyze one or more physical properties of the sample, typically by way of numerical analysis of the thresholded digital image volume. The properties that may be determined in process 220 include bulk elastic properties of the rock. In the context of oil and gas exploration and production, petrophysical properties of interest such as porosity, permeability, formation factor, permeability, relative permeability, electrical conductivity, mercury capillary injection, and the like, may be determined in process 220. These petrophysical properties may be estimated using an appropriate discretization or mesh of the evolved pore space, combined with appropriate numerical simulation, e.g. the direct numerical simulation of single phase fluid flow for computation of absolute permeability. The determination of some of these petrophysical properties in process 220 may also require numerical simulation using finite element methods, finite difference methods, finite volume methods, Lattice Boltzmann methods or any variety of other numerical approaches.

The method of preparing rock samples, and the apparatus for carrying out such preparation, according to embodiments of this invention provides important benefits and advantages, particularly for samples to be subjected to X-ray tomography for direct numerical simulation. Embodiments of this invention enable the preparation of cylindrical rock samples with extremely small cross-sectional diameters, for example diameters of 3 mm or less, which allow extremely high resolution tomographic imaging as is necessary to resolve fine structural detail. These samples can be obtained from a wide range of various rock types, including poorly consolidated or otherwise fragile rock, without significantly degradation of material integrity or pore structure. In addition, embodiments of the invention provide flexibility in the sample preparation process, enabling the cutting of samples having any one of a number of cross-sectional shapes, including those of circular, rectangular, and polygonal cross-sections.

While this invention has been described according to one or more of its embodiments, it is of course contemplated that modifications of, and alternatives to, these embodiments, such modifications and alternatives obtaining the advantages and benefits of this invention, will be apparent to those of ordinary skill in the art having reference to this specification and its drawings. It is contemplated that such modifications and alternatives are within the scope of this invention as subsequently claimed herein.

What is claimed is:

1. A wire cutter apparatus, comprising:
   a table;
   a wire supply drum;
   a guiding roller vertically displaced from the wire supply drum, the guiding roller and the wire supply drum each having an axis parallel with one another;
   cutting wire, wound about the wire supply drum and the guiding roller, and extending from the wire supply drum around the guiding roller and back to the wire supply drum, so that parallel lengths of the cutting wire between the wire supply drum and the guiding roller define a cutting plane;
   a holder for holding a specimen of material to be cut by the cutting wire; and
   a plurality of translation stages movable relative to the table, comprising:
      a feed translation stage, coupled to the holder, movable in a feed direction that is substantially parallel to the cutting plane;
      a first translation stage, coupled to the holder, movable in a first direction at an angle to the feed direction; and
      a second translation stage, coupled to the holder, movable in a second direction at an angle to the feed direction;
   wherein the feed direction, the first direction, and the second direction are coplanar with one another.

2. The apparatus of claim 1, wherein the first and second directions are substantially perpendicular to one another.

3. The apparatus of claim 1, wherein the wire supply drum and guiding roller are mounted at a fixed position relative to the table.

4. The apparatus of claim 1, further comprising:
   a positioning plate fixably mounted to the table;
   wherein each of the feed translation stage and the first and second translation stages are movable relative to the positioning plate.

5. The apparatus of claim 4, wherein the holder comprises:
   jaws for holding the sample; and
   a support coupled to the jaws, and coupled to the feed translation stage so as to be movable with the feed translation stage relative to the positioning plate.

6. The apparatus of claim 1, wherein the plane of the feed direction, first direction, and second direction is orthogonal to the cutting plane.

7. The apparatus of claim 6, wherein the cutting plane is oriented vertically, and the plane of the feed direction, first direction, and second direction is oriented horizontally.

8. The apparatus of claim 6, wherein the cutting plane is oriented horizontally, and the plane of the feed direction, first direction, and second direction is oriented vertically.

9. A wire cutter apparatus, comprising:
   a table;
   a wire supply drum;
   a guiding roller vertically displaced from the wire supply drum, the guiding roller and the wire supply drum each having an axis parallel with one another;
   cutting wire, wound about the wire supply drum and the guiding roller, and extending from the wire supply drum around the guiding roller and back to the wire supply drum, so that parallel lengths of the cutting wire between the wire supply drum and the guiding roller define a cutting plane;
   a holder for holding a specimen of material to be cut by the cutting wire, comprising:
      jaws for holding the sample;
      a support coupled to the jaws, and coupled to the feed translation stage so as to be movable with the feed translation stage relative to the positioning plate; and
      a vertical adjustment plate, for adjusting the vertical position of the jaws relative to the positioning plate;
   a plurality of translation stages movable relative to the table, comprising:
      a feed translation stage, coupled to the holder, movable in a feed direction that is substantially parallel to the cutting plane;

a first translation stage, coupled to the holder, movable in a first direction at an angle to the feed direction; and a second translation stage, coupled to the holder, movable in a second direction at an angle to the feed direction; and a positioning plate fixably mounted to the table;

wherein each of the feed translation stage and the first and second translation stages are movable relative to the positioning plate.

10. A wire cutter apparatus, comprising:

a table;

a wire supply drum;

a guiding roller vertically displaced from the wire supply drum, the guiding roller and the wire supply drum each having an axis parallel with one another;

cutting wire, wound about the wire supply drum and the guiding roller, and extending from the wire supply drum around the guiding roller and back to the wire supply drum, so that parallel lengths of the cutting wire between the wire supply drum and the guiding roller define a cutting plane;

a holder for holding a specimen of material to be cut by the cutting wire, comprising:
  jaws for holding the sample; and
  a support coupled to the jaws, and coupled to the feed translation stage so as to be movable with the feed translation stage relative to the positioning plate;

a plurality of translation stages movable relative to the table, comprising:
  a feed translation stage, coupled to the holder, movable in a feed direction that is substantially parallel to the cutting plane, and comprising:
    a linear translation stage coupled to the support of the holder and to the positioning table; and
    an actuator, coupled to the linear translation stage, for controlling movement of the linear translation stage along the feed direction;

a first translation stage, coupled to the holder, movable in a first direction at an angle to the feed direction; and a second translation stage, coupled to the holder, movable in a second direction at an angle to the feed direction; and a positioning plate fixably mounted to the table;

wherein each of the feed translation stage and the first and second translation stages are movable relative to the positioning plate;

and wherein each of the first and second translation stages comprises:
  a linear translation stage coupled to the positioning table; and
  an actuator for controlling movement of the linear translation stage.

11. The apparatus of claim 10, wherein each of the actuators comprise a micrometer actuator.

12. The apparatus of claim 10, wherein each of the actuators comprise a motorized actuator.

13. The apparatus of claim 12, further comprising:
a programmable controller, coupled to each of the actuators, programmed to control the actuators to move the translation stages according to a pre-programmed sequence.

14. The apparatus of claim 10, wherein the feed translation stage and the first and second translation stages each comprise a modular translation stage;
and wherein the first translation stage is mounted to the positioning plate, the second translation stage is mounted to the first translation stage, and the feed translation stage is mounted to the second translation stage.

15. The apparatus of claim 10, wherein two or more of the feed translation stage and the first and second translation stages comprise an integrated translation stage.

* * * * *